(12) United States Patent
Möller

(10) Patent No.: US 7,254,943 B2
(45) Date of Patent: Aug. 14, 2007

(54) ARRANGEMENT AND METHOD FOR COUPLING AN AIR COMPRESSOR TO THE DRIVING SHAFT OF AN INTERNAL COMBUSTION ENGINE

(75) Inventor: Heribert Möller, Sachsen (DE)

(73) Assignee: MAN Nutzfahrzeuge AG (DE)

( * ) Notice: Subject to any disclaimer, the term of this patent is extended or adjusted under 35 U.S.C. 154(b) by 138 days.

(21) Appl. No.: 11/100,131

(22) Filed: Apr. 6, 2005

(65) Prior Publication Data

US 2005/0217646 A1 Oct. 6, 2005

(30) Foreign Application Priority Data

Apr. 6, 2004 (DE) .................. 10 2004 016 904

(51) Int. Cl.
*F16D 33/10* (2006.01)
(52) U.S. Cl. .......................................... 60/359; 60/409
(58) Field of Classification Search .................. 60/348, 60/359, 409
See application file for complete search history.

(56) References Cited

U.S. PATENT DOCUMENTS

| | | | | |
|---|---|---|---|---|
| 2,299,049 A | * | 10/1942 | Ziebolz | ................. 60/359 |
| 3,247,936 A | * | 4/1966 | Aschauer | ................. 60/359 |
| 4,597,481 A | | 7/1986 | Muller et al. | |
| 5,046,326 A | * | 9/1991 | Havemann et al. | ........... 60/358 |

FOREIGN PATENT DOCUMENTS

| | | |
|---|---|---|
| DE | 1 625 770 | 8/1970 |
| DE | 30 13 024 | 10/1981 |
| GB | 775525 | 5/1957 |
| GB | 897014 | 5/1962 |

* cited by examiner

*Primary Examiner*—F. Daniel Lopez
(74) *Attorney, Agent, or Firm*—Robert W. Becker & Associates; Robert W. Becker

(57) ABSTRACT

An arrangement and method for coupling an air compressor to the driving shaft of an internal combustion engine that is used as the drive engine of a vehicle, wherein the air compressor supplies a pneumatic device. The arrangement contains a controllable turbocoupling, the pump impeller of which can be driven by the driving shaft of the internal combustion engine and that, by means of a fluid in the form of a working medium, drives the turbine wheel that in turn is operatively connected with the shaft of the air compressor that is to be operated.

23 Claims, 3 Drawing Sheets

ARRANGEMENT AND METHOD FOR COUPLING AN AIR COMPRESSOR TO THE DRIVING SHAFT OF AN INTERNAL COMBUSTION ENGINE

BACKGROUND OF THE INVENTION

The present invention relates to an arrangement for coupling or connecting an air compressor to the driving shaft of an internal combustion engine that is used as the drive engine of a vehicle, wherein the air compressor supplies a pneumatic device; the invention also relates to a method of operating such an arrangement.

With vehicles that are common these days, and which have pneumatic devices, the air compressor is coupled directly with the driving shaft of the internal combustion engine via appropriate gearing arrangements.

The quantity of air delivered from the air compressor to the pneumatic device is regulated by excess pressure valves that are disposed in the pneumatic device in such a way that when a maximum pressure is exceeded, the excess air escapes via the indicated excess pressure valves.

Although such arrangements have a simple construction, they do not take into account the minimization of fuel consumption demanded these days, and in addition have the drawback that the characteristic, which results with the reciprocating piston air compressors that are used, of exerting a negative torque, after passing the upper dead center position, due to back expansion, leads to the lifting of the tooth surfaces of prearranged toothed-wheel gearings. This shifting of the tooth surfaces, in turn, is responsible for an extremely undesirable development of noise, and increases the wear of the gears that are involved.

Proceeding from the foregoing factors, it is an object of the present invention to provide an arrangement for coupling the air compressor to the driving shaft of an internal combustion engine that is used as the drive engine of a vehicle, whereby the arrangement minimizes the consumption of fuel of the internal combustion engine and transfers no negative torque. It is a further object of the invention to provide a method for operating the inventive arrangement.

BRIEF DESCRIPTION OF THE DRAWINGS

These and other objects and advantages of the present invention will be described in greater detail subsequently with the aid of the accompanying schematic drawings, in which.

SUMMARY OF THE INVENTION

Figure 1:
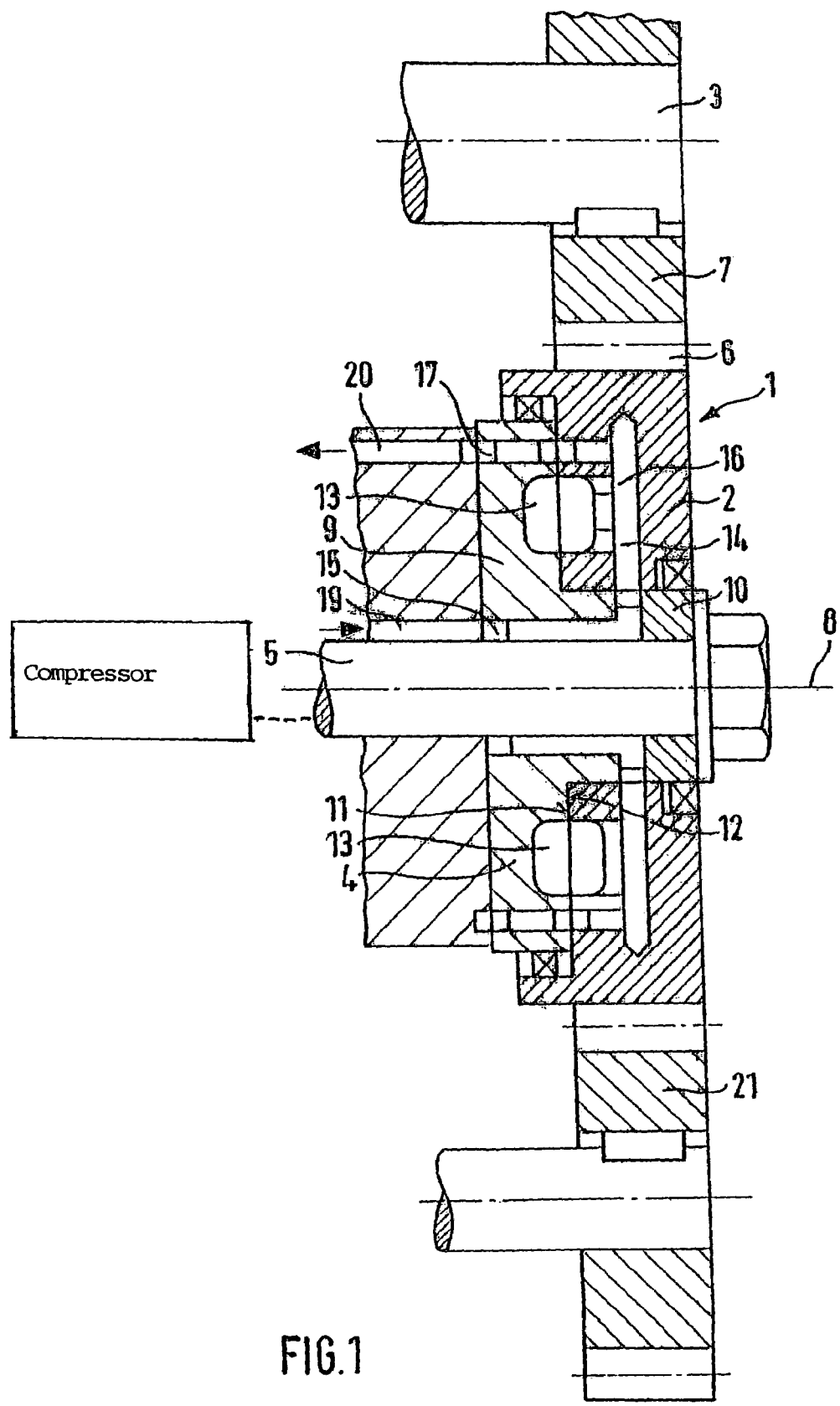
FIG. 1 shows a turbocoupling, as a controllable air compressor drive, that is integrated into a gear wheel of a drive chain.

The arrangement of the present application comprises a controllable turbocoupling that includes a pump impeller, and a turbine wheel that is operatively connected to a driven shaft of the air compressor that is to be operated, wherein the pump impeller can be driven by the driving shaft of the internal combustion engine, and wherein the pump impeller drives the turbine wheel via a fluid in the form of a working or active medium.

The method of operating the arrangement includes interrogating, via a control unit, a pressure sensor that is provided in the pneumatic device, wherein the control unit thereupon determines whether the sensed pressure is below a minimum pressure or exceeds a maximum pressure, wherein if the sensed pressure is below the minimum pressure, the control unit opens a first controllable valve so that the fluid can flow into the control circuit, and wherein if the maximum pressure is exceeded, the control unit closes the first controllable valve and opens a second controllable valve, so that the fluid can flow out of the control circuit.

The realization of the object of the present application is based on the assumption that the arrangement that is provided must take into account an important condition that is implicitedly contained in the statement of the object, namely that the arrangement must have no negative influence upon the driving performance or the driving comfort, as would be the case if torque fluctuations that suddenly occur would make themselves noticeable in sudden accelerations or decelerations, or even only in changes of the noise level of the internal combustion engine.

Taking into account this basic requirement, it was discovered that a hydrodynamic coupling, or also turbocoupling, if it is controllable, due to the delayed build-up of the transferable moment, on the one hand fulfills this implicit basic requirement, and on the other hand realizes the object of the present application.

The use of a controllable turbocoupling as a gearing element between the crankshaft of the internal combustion engine and the air compressor makes it possible, in an advantageous manner, to connect the air compressor as necessary without any sudden fluctuations in torque, and as a consequence thereof sudden slight accelerations or decelerations or sudden changes of the noise level of the internal combustion engine, being noticeable.

Particularly advantageous is the use of a so-called filling or charge controlled turbocoupling, because as a result a precise increase or reduction of the torque transferred by the turbocoupling is possible.

The rotatable mounting of the pump impeller on the shaft that is operatively connected with the air compressor, or, particularly advantageously, on the turbine wheel that is connected with this shaft so as to be fixed against rotation relative thereto, enables a particularly compact construction of the inventive arrangement. Such an arrangement can be selectively embodied as a simple turbocoupling having only one fluid chamber system concentrically disposed in the turbine wheel and pump impeller, or, where there is a requirement that an increased moment can be transferred, as a dual turbocoupling having two fluid chamber systems concentrically disposed in the turbine wheel and pump impeller.

The pump impeller that is driven by the crankshaft of the internal combustion engine, since it is permanently driven, in other words rotates with the crankshaft in a speed ratio that can be defined, is suitable as an intermediate element for the drive of one or more further auxiliary devices of the internal combustion engine, such as steering-assistance pump, generator, etc.

In this connection, it is particularly advantageous if a toothing is provided on the outer periphery of the pump impeller, which toothing on the one hand meshes with a pinion driven by the driving shaft, and on the other hand meshes with the drive pinion of the further auxiliary device, because in this manner the function of the turbocoupling can advantageously be integrated into a gear wheel of a drive chain, and due to the drive moment required by the auxiliary devices already avoids the problem of the tooth surface impact due to the air compressor.

The filling and emptying of the turbocoupling can advantageously be achieved with two controllable valves that are disposed in the fluid circuit of the turbocoupling, whereby the filling is effected over a pressure line, and the emptying is realized by the centrifugal forces that act in the turbocoupling. In this connection, the fluid circuit can advantageously be a portion of the oil circuit or the cooling water circuit of the internal combustion engine.

The arrangement for coupling the air compressor is advantageously operated pursuant to a method that on the one hand connects the turbocoupling as a function of the pressure in the compressed air system, which contributes to a minimization of the fuel requirement, and on the other hand controls the filling of the turbocoupling such that the air compressor can transfer no noticeable negative torque, in other words a torque counter to the drive direction of rotation of the air compressor that is effected by back expansion in the compression chamber of the air compressor. In addition to a design of the fluid chambers that is optimized for this purpose, this can be advantageously achieved in that the turbocoupling is either operated permanently, or particularly advantageously only if the negative torque occurs, with enough slip that a transfer of this negative torque does not take place due to the turbocoupling.

Further specific features of the present application will be described in detail subsequently.

DESCRIPTION OF SPECIFIC EMBODIMENTS

Referring now to the drawings in detail, provided for driving an air compressor is, as schematically illustrated in FIG. 1, a turbine-driven coupling or turbocoupling 1, the turbine wheel 4 of which is seated on the shaft 5 that operates the air compressor (not illustrated) so as to be fixed against rotation relative thereto. The turbine wheel 4 is provided with a first portion 9 having a large diameter, and a second portion 10 having a small diameter. The pump impeller or rotor 2 of the turbocoupling 1 is embodied as an annular body of rotation and, via its inner diameter, rotatably rests upon the second portion 10 of the turbine wheel 4 in such a way that the facing lateral surfaces 11, 12 of the turbine wheel 4 and of the pump impeller 2 directly adjoin one another. Disposed in the turbine wheel 4 and the pump impeller 2, concentrically relative to the axis of rotation 8 and essentially in halves, with their halves being disposed opposite one another, are fluid chambers 13 that respectively extend through the adjacent lateral surfaces 12, 11 of the pump impeller 2 and of the first portion 9 of the turbine wheel 4. The fluid is supplied to the fluid chambers 13 via a fluid supply channel 19 that is fixedly supported on the air compressor, and passes via the peripheral fluid supply groove 15 and the fluid feed channels 14 into the fluid chambers 13, which form the working chamber of the turbocoupling 1. For the emptying of the turbocoupling 1, fluid withdrawal channels 16 are provided that are also connected with the fluid chambers 13 and that withdraw the fluid out of the fluid chambers via a fluid removal groove 17 and a fluid withdrawal channel 20 that is fixedly supported on the air compressor.

The drive of the arrangement is effected via the driving shaft 3 of the internal combustion engine (not illustrated). For this purpose, disposed on the driving shaft 3 is a pinion 7 that meshes with teeth 6 disposed on the outer periphery of the pump impeller 2. By means of the teeth 6, a drive pinion 21 that meshes therewith is driven, which in turn acts upon a further auxiliary device and operates the same. The auxiliary device can, for example, be the steering-assistance pump, the generator, or the like.

Figure 2:
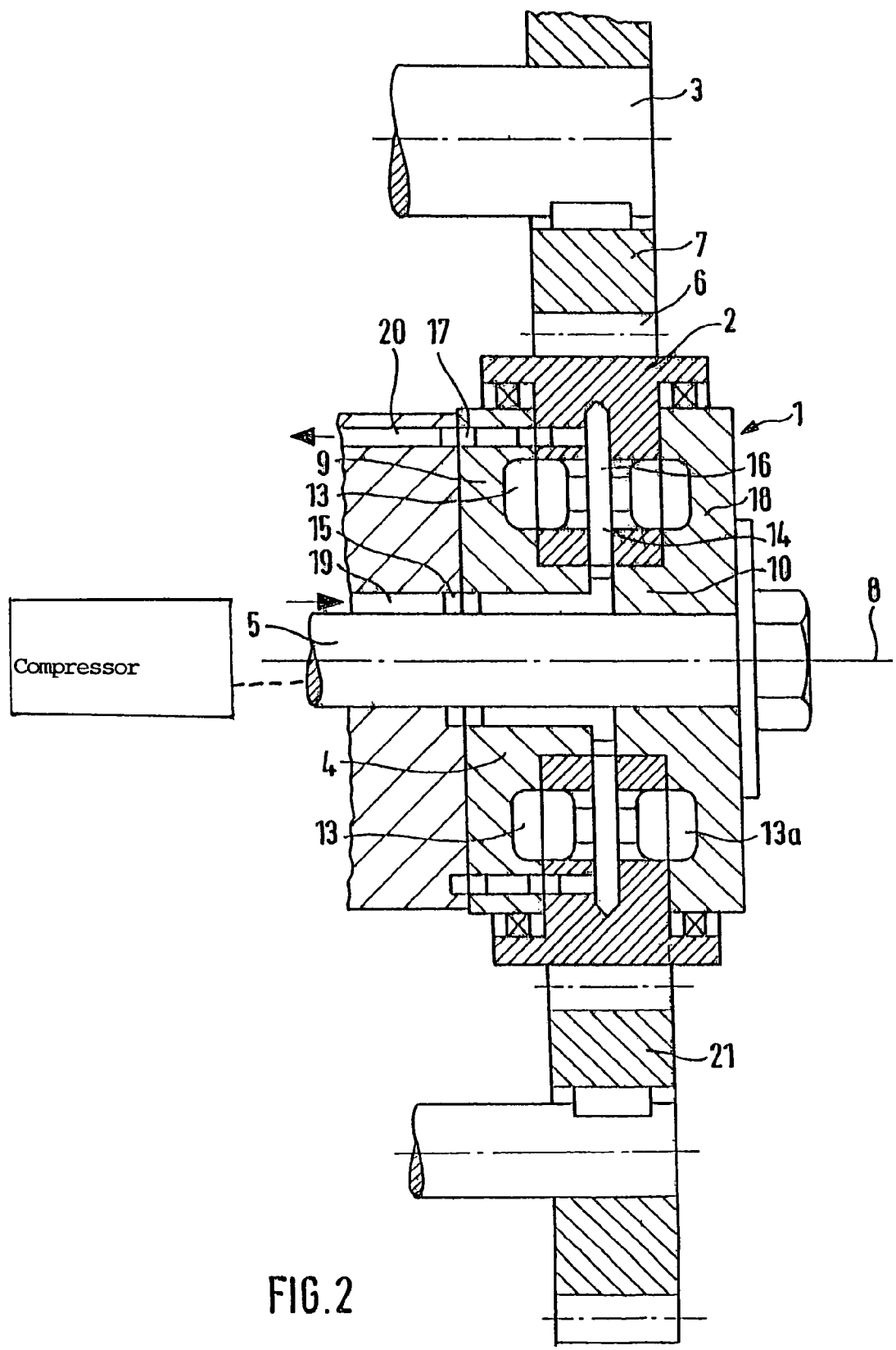
FIG. 2 shows the embodiment of FIG. 1 in the form of a dual turbocoupling.

An embodiment that is expanded relative to the embodiment of FIG. 1 is again schematically illustrated in FIG. 2. Since except for the indicated expansion the embodiment illustrated in FIG. 2 is identical to the arrangement of FIG. 1, reference is made to the description of FIG. 1 with regard to the description of these identical components.

The arrangement of FIG. 2 involves a dual turbocoupling. This means that two parallel fluid chamber systems are operative at the same time. For this purpose, in addition to the first portion 9 and the second portion 10, a third portion 18 is associated with the body of rotation that forms the turbine wheel 4; the diameter of the third portion 18 essentially corresponds to the diameter of the first portion 9. Since the second portion 10 of the turbine wheel 4 must be accessible for mounting of the pump impeller 2, the turbine wheel 4 is split into 2 partial bodies, whereby the non-illustrated plane of separation, which intersects the axis of rotation 8, is disposed in the second portion 10 of the turbine wheel 4. If the pump impeller 2 is now rotatably disposed upon the second portion 10, a second fluid chamber system can be realized parallel to the first fluid chamber system in that further fluid chambers 13a are disposed in the third portion 18 of the turbine wheel 4 and in the oppositely disposed portion of the pump impeller, essentially half in each, such that they extend concentrically relative to the axis of rotation 8, are disposed opposite one another, and respectively extend through adjacent surfaces of the pump impeller 2 and of the third portion 18 of the turbine wheel 4.

The advantage of a dual turbocoupling is obvious. The doubled torque can be realized with only slightly greater outer dimensions.

The arrangements described in conjunction with FIGS. 1 and 2 are characterized in that the turbocoupling is integrated into a gear wheel and hence, on the one hand, becomes an element in a transmission or drive chain in the nature of a simple gear, but at the same time can be controlled, and with a controllable transmission characteristic derives the drive moment for the air compressor from this drive chain.

Figure 3:
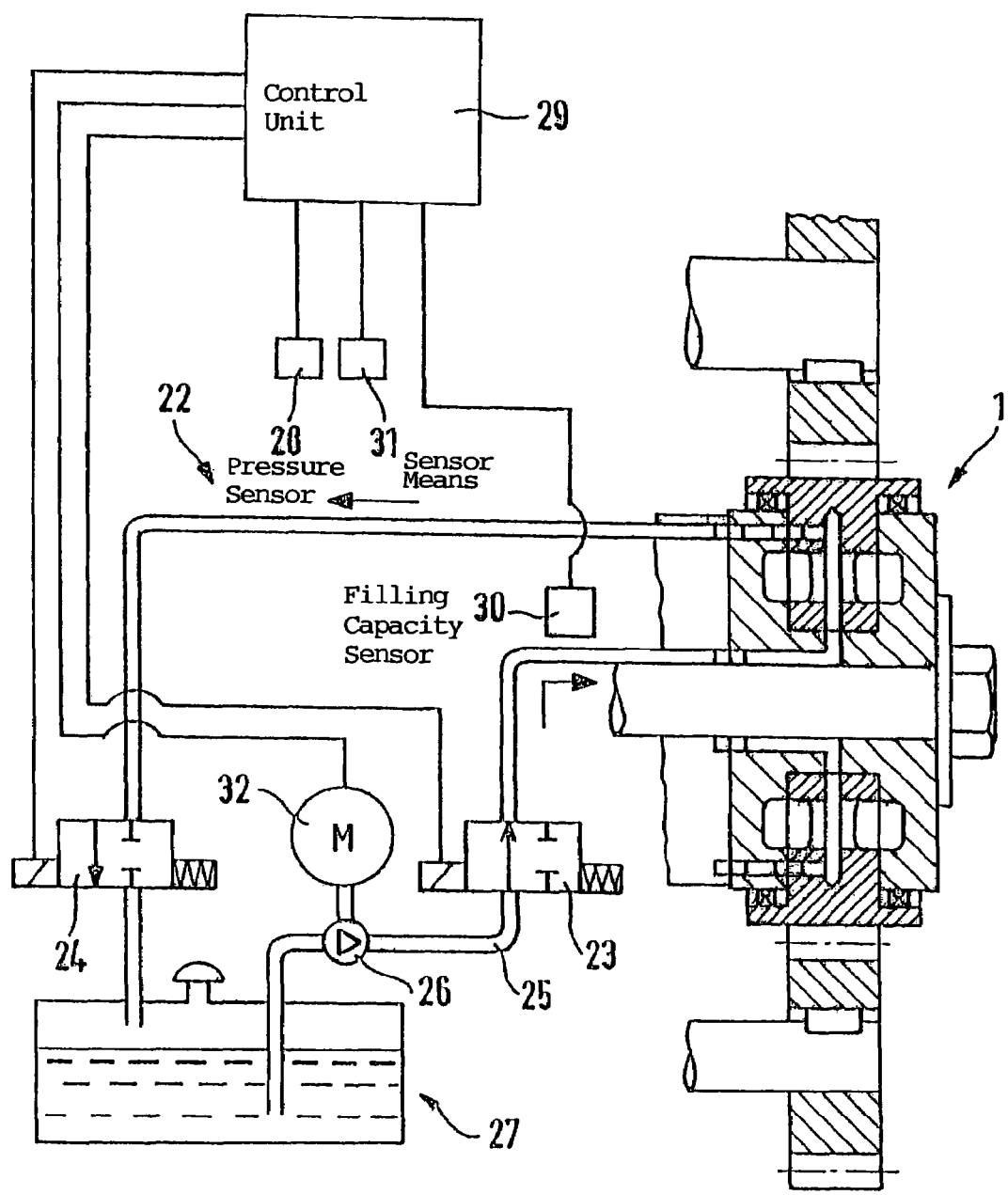
FIG. 3 shows a fluid circuit for controlling the turbocoupling of FIG. 2.

The inventive method for operating the arrangement described above, and hence its manner of operation, will be described in greater detail subsequently with the aid of FIG. 3 and, where necessary, FIG. 2.

As already mentioned, the inventive arrangement serves for the connection of the air compressor of a vehicle that is equipped with a pneumatic device and is operated via an internal combustion engine, as a function of the actual compressed air requirement, in order to minimize the fuel requirement of the vehicle. The following description is based on the assumption that the internal combustion engine is operating.

As previously mentioned, the turbocoupling 1 serves in a known manner to transmit torques of a fluid, as a working medium, that is supplied via an external fluid circuit 22 of the turbocoupling 1. Starting from a supply container 27 and via a pump 26, a pressure line 25, a first controllable valve 23 and possibly further lines, the fluid circuit 22 leads to the fluid supply channel 19, which is fixedly connected with the air compressor and which in turn communicates via the fluid supply groove 15 and the fluid feed channel 14 with the fluid chambers 13, 13a. To empty the turbocoupling 1, fluid withdrawal channels 16 lead back from the fluid chambers 13, 13a to the supply container 27 via the fluid removal groove 17, the fluid withdrawal channel 20 that is fixedly connected with the air compressor, as well as possibly further lines and a second controllable valve 24.

As already mentioned, the fluid circuit 22 can be part of the oil circuit or part of the cooling water circuit of the internal combustion engine. In this case, the pump 26 that is provided for conveying the fluid is either the oil pump or the cooling water pump of the internal combustion engine. If the fluid used in the turbocoupling is a special medium, a separate drive, for example a motor 32, is required for operating the pump 26.

For controlling the operation of the air compressor, a control unit 29 is provided that is formed by the electronic vehicle control used in vehicles that are common these days, or it can be a partial component thereof.

By means of the control unit 29, when the internal combustion engine is being operated, a pressure sensor 28 that is disposed in the pneumatic device is cyclically interrogated and the thus determined measured value, which is proportional to the actual pressure in the pneumatic device is compared with a stored minimum value or maximum value respectively. If the comparison shows a dropping below the stored minimum value, the control unit 29 opens the first controllable valve 23, so that the fluid, which is conveyed by the pump 26 out of the supply container 27 and into the pressure line 25, passes into the fluid chambers 13, 13a via this valve, the fixedly connected fluid supply channel 19, the fluid supply groove 15, and the fluid feed channel 14. At this point in time, the second controllable valve 24 is closed, so that the fluid chambers 13, 13a fill with the fluid, in other words the working medium. As the filling level in the fluid chambers 13, 13a rises, the turbocoupling 1 begins to transfer torque or moments of rotation to the shafts 5 that are operatively connected to the air compressor, as a result of which the latter smoothly starts up as slip in the turbocoupling 1 decreases. Due to the smooth start-up, all abrupt changes in torque are avoided; the connection of the air compressor thus has no noticeable influence upon the driving performance or noise level of the vehicle.

The filling capacity of the fluid circuit is regulated by the control unit 29, via a filling capacity sensor 30 that can be embodied, for example, as a flow volume gauge in a fluid supply line or, in a simplified embodiment, as a timing element that determines the opening time of the first controllable valve 23, in such a way that the quantity of fluid disposed in the turbocoupling 1 permits a prescribed slip in the turbocoupling in order to prevent the previously mentioned negative torque that occurs with reciprocating piston air compressors from being transferred from the turbocoupling 1. This can be reinforced in an alternative embodiment by always briefly reducing the filling capacity of the turbocoupling 1 when the negative torque occurs. This is realized by briefly opening the second controllable valve 24 for the emptying and briefly opening the first controllable valve 23 for the refilling via the control unit 29. The point in time at which the opening and closing of the second controllable valve 24 or the first controllable valve 23 is effected is determined by the control unit 29 by monitoring the operating cycle of the air compressor. For this purpose, sensor means 31, for example in the form of a sensor for determining angle of rotation, is used via which the control unit 29, which is connected therewith, detects the point in time at which the negative torque, which occurs after the piston of the air compressor passes the upper dead center point, is to be compensated for. When the second controllable valve 24 opens, the turbocoupling empties very rapidly due to the effective centrifugal forces, so that by a rapid changing of the valves 23, 24, the reduction of the filling capacity of the turbocoupling 1 can be limited to very short time spans.

If the control unit 29, via the pressure sensor 28, detects that the maximum permissible pressure in a pneumatic device of the vehicle has been exceeded, an emptying of the turbocoupling 1 is effected by opening the second controllable valve 24 via the control unit 29. Not only during the filling process, but also during the emptying process, the speed of filling or emptying can be adapted to the desired activation or deactivation characteristic of the air compressor by timed control of the first controllable valve 23 or of the second controllable valve 24.

It should finally be noted that the connection or disconnection of the air compressor can also be effected as a function of further operating perimeters of the pneumatic device of the internal combustion engine, or of the air compressor itself; for this purpose, it is merely necessary to provide a connection of the control unit 29 to appropriate sensors influenced by these components, and/or to the control arrangements of these components.

If the working medium used in the turbocoupling 1 is neither the oil from the oil circuit nor the cooling water from the cooling water circuit of the internal combustion engine, but rather is a special fluid, the drive of the pump 26 is effected by a separate motor 32 that is then controlled by the control unit 29 as a function of a delivery requirement that is present.

The previously described examples, as well as the arrangement and also the method of operating the arrangement, can, of course, be embodied in many different ways with structural measures available to one of skill in the art without thereby deviating from the basic inventive concept, so that the embodiments described are presented by way of example only.

The specification incorporates by reference the disclosure of priority document 10 2004 016 904.7 of Apr. 6, 2004.

The present invention is, of course, in no way restricted to the specific disclosure of the specification and drawings, but also encompasses any modifications within the scope of the appended claims.

The invention claimed is:

1. An arrangement for coupling an air compressor to the driving shaft of an internal combustion engine that is used as the drive engine of a vehicle, wherein the air compressor supplies a pneumatic device, said arrangement comprising:

a controllable turbocoupling that includes a pump impeller, and a turbine wheel that is operatively connected to a driven shaft of the air compressor that is to be operated, wherein said pump impeller can be driven by said driving shaft of the internal combustion engine, wherein said pump impeller drives said turbine wheel via a fluid in the form of a working medium, wherein said turbine wheel is disposed on said driven shaft that is operatively connected with said air compressor such that said turbine wheel is fixed against rotation relative to said driven shaft, and wherein said pump impeller is rotatably mounted on said turbine wheel or on the shaft that is operatively connected to said air compressor, and is operatively connected with said driving shaft of the internal combustion engine, wherein said turbine wheel is formed by a first body of rotation that, when viewed in a direction of its axis of rotation, comprises at least two portions, wherein a first portion has a large diameter and a second portion has a diameter that is smaller than that of the first portion, wherein said pump impeller is formed by an annular body of rotation that is rotatably disposed on said turbine wheel in said second portion having the small diameter in such a way that respective lateral surfaces of said turbine wheel and said pump impeller respectively are directly adjacent to one another, wherein fluid chambers of said turbocoupling are disposed in said first portion of said turbine wheel and in said pump impeller, concentric to an axis of rotation of said turbocoupling, and essentially in halves, wherein the halves of said fluid chambers are disposed opposite one another and respectively extend through said adjacent lateral surfaces of said pump impeller and of said first portion of said turbine wheel, wherein at least one fluid feed channel is provided that is supplied from a fluid supply groove disposed in the vicinity of said driven shaft and that in turn supplies fluid to said fluid chambers, and wherein at least one fluid withdrawal channel is provided that withdraws the fluid from said fluid chambers into a fluid removal groove that is disposed remotely from said driven shaft.

2. An arrangement according to claim 1, wherein said controllable turbocoupling is a turbocoupling that is controlled by adjustably filling the turbocoupling.

3. An arrangement according to claim 1, wherein said controllable turbocoupling can be filled with a fluid via a fluid circuit, wherein a first controllable valve is provided in said fluid circuit for a filling operation, and wherein an emptying of said turbocoupling is effected via a second controllable valve of said fluid circuit.

4. An arrangement according to claim 3, wherein said filling is effected via a pressure line, and wherein said fluid is conveyed out of a supply container, via a pump, and is supplied under pressure into said pressure line.

5. An arrangement according to claim 3, wherein said fluid circuit is a portion of an oil circuit for lubrication of the internal combustion engine.

6. An arrangement according to claim 1, wherein said body of rotation that forms said turbine wheel is provided with a third portion as viewed in the direction of said axis of rotation, wherein said third portion has a diameter that corresponds approximately to the diameter of said first portion, wherein said turbine wheel is split into two partial bodies, wherein a plane of separation intersects said axis of rotation and extends in said second portion having the small diameter, wherein said pump impeller is rotatably disposed between said first portion and said third portion of said turbine wheel, wherein a respective one of said lateral surfaces of said pump impeller is respectively disposed directly adjacent to an inwardly disposed lateral surface of said first portion and said third portion of said turbine wheel, wherein further fluid chambers are provided concentrically relative to said axis of rotation in said third portion of said turbine wheel and in said pump impeller, essentially in halves and opposite one another, and wherein said further fluid chamber extend through respective adjacent lateral surfaces of said pump impeller and of said third portion of said turbine wheel.

7. An arrangement according to claim 1, wherein a fixedly supported fluid supply channel communicates with said fluid supply groove, wherein a fixedly supported fluid withdrawal channel communicates with said fluid removal groove, and wherein a fluid circuit is provided that communicates with said fluid supply channel and with said fluid withdrawal channel, via which fluid circuit said fluid chambers, in an externally controlled manner, can be filled and emptied.

8. An arrangement according to claim 1, wherein said pump impeller is operatively connected with at least one further auxiliary device that is to be driven by said driving shaft of the internal combustion engine.

9. An arrangement according to claim 1, wherein said pump impeller is provided on an outer periphery thereof with teeth that mesh with a pinion driven by said driving shaft of the internal combustion engine.

10. An arrangement according to claim 9, wherein at least one further auxiliary device can be driven by a drive pinion that meshes with said teeth of said pump impeller.

11. An arrangement, for coupling an air compressor to the driving shaft of an internal combustion engine that is used as the drive engine of a vehicle, wherein the air compressor supplies a pneumatic device, said arrangement comprising:
a controllable turbocoupling that includes a pump impeller, and a turbine wheel that is operatively connected to a driven shaft of the air compressor that is to be operated, wherein said pump impeller can be driven by said driving shaft of the internal combustion engine, and wherein said pump impeller drives said turbine wheel via a fluid in the form of a working medium, wherein said controllable turbocoupling can be filled with a fluid via a fluid circuit, wherein a first controllable valve is provided in said fluid circuit for a filling operation, and wherein an emptying of said turbocoupling is effected via a second controllable valve of said fluid circuit and wherein said fluid circuit is a portion of a water circuit for cooling of the internal combustion engine.

12. An arrangement according to claim 11, wherein said turbine wheel is disposed on said driven shaft that is operatively connected with said air compressor such that said turbine wheel is fixed against rotation relative to said driven shaft, and wherein said pump impeller is rotatably mounted on said turbine wheel or on the shaft that is operatively connected to said air compressor, and is operatively connected with said driving shaft of the internal combustion engine.

13. An arrangement according to claim 12, wherein said turbine wheel is formed by a first body of rotation that, when viewed in a direction of its axis of rotation, comprises at least two portions, wherein a first portion has a large diameter and a second portion has a diameter that is smaller than that of the first portion, wherein said pump impeller is formed by an annular body of rotation that is rotatably disposed on said turbine wheel in said second portion having the small diameter in such a way that respective lateral surfaces of said turbine wheel and said pump impeller respectively are directly adjacent to one another, wherein fluid chambers of said turbocoupling are disposed in said first portion of said turbine wheel and in said pump impeller, concentric to an axis of rotation of said turbocoupling, and essentially in halves, wherein the halves of said fluid chambers are disposed opposite one another and respectively extend through said adjacent lateral surfaces of said pump impeller and of said first portion of said turbine wheel, wherein at least one fluid feed channel is provided that is supplied from a fluid supply groove disposed in the vicinity of said driven shaft and that in turn supplies fluid to said fluid chambers, and wherein at least one fluid withdrawal channel is provided that withdraws the fluid from said fluid chambers into a fluid removal groove that is disposed remotely from said driven shaft.

14. An arrangement according to claim 13, wherein said body of rotation that forms said turbine wheel is provided with a third portion as viewed in the direction of said axis of rotation, wherein said third portion has a diameter that corresponds approximately to the diameter of said first portion, wherein said turbine wheel is split into two partial bodies, wherein a plane of separation intersects said axis of rotation and extends in said second portion having the small diameter, wherein said pump impeller is rotatably disposed between said first portion and said third portion of said turbine wheel, wherein a respective one of said lateral surfaces of said pump impeller is respectively disposed directly adjacent to an inwardly disposed lateral surface of said first portion and said third portion of said turbine wheel, wherein further fluid chambers are provided concentrically relative to said axis of rotation in said third portion of said turbine wheel and in said pump impeller, essentially in halves and opposite one another, and wherein said further fluid chamber extend through respective adjacent lateral surfaces of said pump impeller and of said third portion of said turbine wheel.

15. An arrangement according to claim 13, wherein a fixedly supported fluid supply channel communicates with said fluid supply groove, wherein a fixedly supported fluid withdrawal channel communicates with said fluid removal groove, and wherein a fluid circuit is provided that communicates with said fluid supply channel and with said fluid withdrawal channel, via which fluid circuit said fluid chambers, in an externally controlled manner, can be filled and emptied.

16. An arrangement according to claim 12, wherein said pump impeller is operatively connected with at least one further auxiliary device that is to be driven by said driving shaft of the internal combustion engine.

17. An arrangement according to claim 12, wherein said pump impeller is provided on an outer periphery thereof with teeth that mesh with a pinion driven by said driving shaft of the internal combustion engine.

18. An arrangement according to claim 17, wherein at least one further auxiliary device can be driven by a drive pinion that meshes with said teeth of said pump impeller.

19. An arrangement according to claim 11, wherein said controllable turbocoupling is a turbocoupling that is controlled by adjustably filling the turbocoupling.

20. An arrangement according to claim 11, wherein said filling is effected via a pressure line, and wherein said fluid is conveyed out of a supply container, via a pump, and is supplied under pressure into said pressure line.

21. A method of operating an arrangement for coupling an air compressor to the driving shaft of an internal combustion engine that is used as the drive engine of a vehicle, wherein the air compressor supplies a pneumatic device, said method including the steps of:
providing a pressure sensor in said pneumatic device;
interrogating said pressure sensor via a control unit, wherein said control unit thereupon determines whether a sensed pressure is below a minimum pressure or exceeds a maximum pressure;
providing a first controllable valve in a fluid circuit, wherein if the sensed pressure is below the minimum pressure said control unit opens said first controllable valve, so that fluid can flow into said fluid circuit; and
providing a second controllable valve in said fluid circuit, wherein if said maximum pressure is exceeded, said control unit closes said first controllable valve and opens said second controllable valve so that fluid can flow out of said fluid circuit, wherein a filling capacity sensor is disposed in said fluid circuit and is cyclically interrogated by said control unit for determining an actual quantity of filling, and wherein said control unit controls the filling quantity via said first and second controllable valves as a function of operating parameters of at least one of the internal combustion engine, the air compressor, and the pneumatic device, which operating parameters are detected by said control unit.

22. A method of operating an arrangement for coupling an air compressor to the driving shaft of an internal combustion engine that is used as the drive engine of a vehicle, wherein the air compressor supplies a pneumatic device, said method including the steps of:
providing a pressure sensor in said pneumatic device;
interrogating said pressure sensor via a control unit, wherein said control unit thereupon determines whether a sensed pressure is below a minimum pressure or exceeds a maximum pressure;
providing a first controllable valve in a fluid circuit, wherein if the sensed pressure is below the minimum pressure said control unit opens said first controllable valve, so that fluid can flow into said fluid circuit; and
providing a second controllable valve in said fluid circuit, wherein if said maximum pressure is exceeded, said control unit closes said first controllable valve and opens said second controllable valve so that fluid can flow out of said fluid circuit, wherein the air compressor is a reciprocating piston air compressor, and wherein said control unit monitors the operating cycle of said air compressor via sensor means and in each operating cycle, shortly before the reciprocating piston of the air compressor reaches its upper dead center position, briefly reduces the filling quantity of said fluid circuit via said controllable valves such that said turbocoupling can transfer no noticeable torque in the direction of rotation that is opposite a drive direction of rotation of the air compressor.

23. A method of operating an arrangement for coupling an air compressor to the driving shaft of an internal combustion engine that is used as the drive engine of a vehicle, wherein the air compressor supplies a pneumatic device, said method including the steps of:
providing a pressure sensor in said pneumatic device;
interrogating said pressure sensor via a control unit, wherein said control unit thereupon determines whether a sensed pressure is below a minimum pressure or exceeds a maximum pressure;
providing a first controllable valve in a fluid circuit, wherein if the sensed pressure is below the minimum pressure said control unit opens said first controllable valve, so that fluid can flow into said fluid circuit; and
providing a second controllable valve in said fluid circuit, wherein if said maximum pressure is exceeded, said control unit closes said first controllable valve and opens said second controllable valve so that fluid can flow out of said fluid circuit, wherein the air compressor is a reciprocating piston air compressor, and wherein said control unit maximally increases a filling quantity of said fluid circuit only to such an extent that due to the thereby resulting slip of said turbocoupling the latter is not in a position to transfer torque that briefly occurs counter to a driving direction of the air compressor.

* * * * *